United States Patent
Kang et al.

(10) Patent No.: US 8,841,426 B2
(45) Date of Patent: Sep. 23, 2014

(54) MUTANT OF GRANULOCYTE-COLONY STIMULATING FACTOR (G-CSF) AND CHEMICALLY CONJUGATED POLYPEPTIDE THEREOF

(75) Inventors: Kwan-Yub Kang, Yongin-si (KR); Jeong-Woon Hong, Hanam-si (KR)

(73) Assignee: Mogam Biotechnology Research Institute, Yongin-si (KR)

( * ) Notice: Subject to any disclaimer, the term of this patent is extended or adjusted under 35 U.S.C. 154(b) by 1218 days.

(21) Appl. No.: 11/995,968

(22) PCT Filed: Jul. 19, 2006

(86) PCT No.: PCT/KR2006/002841
§ 371 (c)(1),
(2), (4) Date: Jan. 17, 2008

(87) PCT Pub. No.: WO2007/011166
PCT Pub. Date: Jan. 25, 2007

(65) Prior Publication Data
US 2008/0200657 A1    Aug. 21, 2008

(30) Foreign Application Priority Data

Jul. 20, 2005  (KR) ................. 10-2005-0065746

(51) Int. Cl.
*A61K 38/24* (2006.01)
*C07K 1/00* (2006.01)
*C07K 14/535* (2006.01)
*A61K 47/48* (2006.01)

(52) U.S. Cl.
CPC ......... *C07K 14/535* (2013.01); *A61K 47/48215* (2013.01)
USPC .......................................... 530/399; 530/350

(58) Field of Classification Search
None
See application file for complete search history.

(56) References Cited

U.S. PATENT DOCUMENTS

| | | |
|---|---|---|
| 4,810,643 A | 3/1989 | Souza |
| 5,104,651 A | 4/1992 | Boone et al. |
| 5,643,575 A | 7/1997 | Martinex et al. |
| 5,824,784 A | 10/1998 | Kinstler et al. |
| 5,849,883 A | 12/1998 | Boone et al. |
| 5,939,280 A | 8/1999 | Nobuo et al. |
| 5,985,265 A | 11/1999 | Kinstler et al. |
| 6,113,906 A | 9/2000 | Greenwald et al. |
| 6,555,660 B2 | 4/2003 | Nissen et al. |
| 6,602,498 B2 | 8/2003 | Shen |
| 6,646,110 B2 | 11/2003 | Nissen et al. |
| 6,753,165 B1 | 6/2004 | Cox et al. |
| 6,831,158 B2 | 12/2004 | Nissen et al. |
| 7,309,781 B2 | 12/2007 | Cox, III |
| 2004/0175800 A1 | 9/2004 | Cox, III et al. |
| 2005/0058620 A1 | 3/2005 | Nakamoto et al. |
| 2005/0143563 A1 | 6/2005 | Park et al. |
| 2005/0147587 A1 | 7/2005 | Nissen et al. |
| 2006/0084793 A1 | 4/2006 | Nissen et al. |

FOREIGN PATENT DOCUMENTS

| | | |
|---|---|---|
| EP | 0727438 A2 | 8/1996 |
| JP | 08-165300 A | 6/1996 |
| JP | 09-506116 A | 6/1997 |
| JP | 2003-519478 A | 6/2003 |
| WO | 01/51510 A2 | 7/2001 |
| WO | 03/078461 A1 | 9/2003 |

OTHER PUBLICATIONS

Brems. 2002. Protein Science 11:2504-2511.*
Doherty, D.H., et al., "Site-Specific PEGylation of Engineered Cysteine Analogs of Recombinant Human Granulocyte-Macrophage Colony-Stimulating Factor," Bioconjug Chem., 2005, 16(5): 1291-1298.

* cited by examiner

*Primary Examiner* — Shulamith H Shafer
(74) *Attorney, Agent, or Firm* — Sughrue Mion, PLLC

(57) ABSTRACT

Provided are mutants of human granulocyte-colony stimulating factor (G-CSF) designed for specific chemical conjugation, and chemical conjugates thereof for use as an adjuvant in the treatment of cancer. The present invention provides a mutant of a G-CSF in which a threonine (Thr) residue at position 133 of G-CSF comprising the amino acid sequence identified in SEQ ID NO: 1 is substituted with a cysteine (Cys) residue. In addition, the invention provides a mutant of a G-CSF in which a cysteine (Cys) residue is inserted between a glycine (Gly) residue at position 135 and an alanine (Ala) residue at position 136 of G-CSF. Further, the invention provides a chemically conjugated mutant G-CSF to which biocompatible polymer such as polyethylene glycol (PEG) was attached at the cysteine residue, which was introduced by the substitution or insertion mutation, increasing its in vivo retention time without reducing in vivo biological activity due to the conjugation with the biocompatible polymer, thereby ultimately extending the in vivo biological activity.

6 Claims, 3 Drawing Sheets

MUTANT OF GRANULOCYTE-COLONY STIMULATING FACTOR (G-CSF) AND CHEMICALLY CONJUGATED POLYPEPTIDE THEREOF

TECHNICAL FIELD

The present invention relates to a mutant of human granulocyte-colony stimulating factor (G-CSF) and chemical conjugate thereof as an adjuvant in the treatment of cancer for inhibiting the leukocytopenia by stimulating the formation of neutrophilic granulocyte colonies from bone marrow cells when an anticancer drug is administered, and inducing the differentiation of the bone marrow cells to final stage, and more particularly, to a mutant of human granulocyte-colony stimulating factor (G-CSF) modified by substitution or insertion of an amino acid at a specific site on the G-CSF and chemical conjugate thereof with a nonprotein polymer such as polyethylene glycol (PEG).

BACKGROUND ART

Human hematopoietic activities are carried out primarily in the bone marrow and various kinds of blood cells are produced through a variety of complex pathways. The hematopoietic activities are controlled by specific glycoproteins, which are generally referred to as colony stimulating factors (CSFs). CSFs have been identified and distinguished according to their activities. That is to say, CSFs, which serve as growth factors when blood cells are cultured in semi-solid media, stimulate the clonal formation of monocytes, granulocytes or other hematopoietic cells. For example, granulocyte-CSF (G-CSF) and macrophage-CSF (M-CSF) stimulate the in vitro formation of neutrophilic granulocyte and macrophage colonies, respectively while multi-CSF, also known as interleukin-3 (IL-3), stimulates the clonal proliferation of various types of blood and tissue cells, such as granulocyte, macrophages, megakaryocytes, red blood cells, or the like.

Specifically, the G-CSF, which is a cytokine of instructing the division and differentiation of intermedullary stem cells and leukocytes outside the bone marrow, has been known to promote the phagocytic activity of neutrophils by stimulating the differentiation and/or proliferation of neutrophil progenitor cells and activating mature neutrophils, and the reactivity to chemotactic factors ((Metcalf, Blood) 67:257 (1986); (Yan, et al., Blood) 84(3): 795-799 (1994); (Bensinger, et al., Blood) 81(11):3158-3163 (1993); (Roberts, et al., Expt'l Hematology) 22:1156-1163 (1994); (Neben, et al., Blood) 81(7): 1960-1967 (1993)).

Treatment of malignant tumors is generally performed by radiotherapy and/or chemotherapy, which undesirably result in a sharp reduction of leukocytes and lowered immunity occurring incidental to the reduction of leukocytes, thereby causing significant drawbacks when the therapeutic treatment by radiotherapy and/or chemotherapy is performed over an extended period of time. G-CSFs were initially reported as adjuvants capable of effectively treating the cancer by activating a patient's immunizing capability (Lopez et al., J. Immunol. 131(6):2983-2988, 1983; Platzer et al., J. Exp. Med. 162:1788-1801, 1985), and are currently effectively used for the treatment of a variety of cancers and intractable leukemia.

Research of G-CSFs started initially with the finding that granulocyte-CSF materials are present in the culture medium of human carcinoma CHU-2 cell line (Nomura et al, EMBO J. 8(5):871-876, 1986) or human bladder carcinoma cell line 5637 (Welte et al., Proc. Narl. Acad. Sci. USA82:1526-1530, 1985; Strige et al., Blood 69(5):1508-1523, 1987), and a protein having granulocyte-colony stimulating activity having a molecular weight of 18 to 19 kDa was purified (Nomura et al., EMBO J. 5(5):871-876, 1986).

The cDNAs of G-CSFs were first isolated from human bladder carcinoma cell line 5673 by L. M. Souza et al. (Science, 232: 61-65 (1986) (see Korean Patent Publication No. 1998-77885), and then cloned from cDNA libraries of squamous carcinoma cell line and peripheral blood macrophage (S, Nagata et al., Nature, 319: 415-417 (1986); S, Nagata et al., EMBO J., 5: 575-581 (1986); Y. Komatsu et al., Jpn. J. Cancer Res., 78: 1179-1181 (1987)).

With the advent of gene recombinant technology, it was revealed that G-CSFs are produced as insoluble inclusion bodies in the course of expressing a large amount of G-CSF from *Escherichia coli* and converted into active G-CSFs by refolding. The recombinant G-CSF (rG-CSF) produced from *E. coli* comprises a protein identified in SEQ ID NO:2 (175 amino acids), that is, a natural G-CSF (174 amino acids) identified in SEQ ID NO:1 and N-terminal methionine, and has a molecular weight of about 19 kDa.

In addition, the natural G-CSF has an O-glycosylation site in an amino acid threonine (Thr) at position No. 133 while the rG-CSF derived from *E. coli* has no glycosylation site. However, it is known that the presence or absence of the glycosylation site and/or N-terminal methionine have little effect on the biological activity (Souza et al.: Science 232, 1986, 61).

Biological protein therapeutic agents such as G-CSF have advantageously high selectivity and low toxicity while they have a short in vivo retention time and are unstable. To overcome such drawbacks, there has been developed a method of conjugating biocompatible polymers, e.g., polyethylene glycol (PEG), polyvinyl alcohol (PVA) or polyvinyl pyrrolidone, to biological proteins (polypeptides), e.g., G-CSF or interferon. Such PEG conjugation prevents degradation of biological proteins by effectively inhibiting proteases, increases the stability and half life of a biological protein therapeutic agent by preventing fast excretion of the biological protein therapeutic agent from the kidney, and reducing the immunogenicity (Sada et al. J. Fermentation Bioengineering 71: 137-139 (1991)).

In particular, examples of the PEGylated protein therapeutic agents include a pegylated formulation of adenosine diaminase developed as a therapeutic agent of combined immunodeficiency; a pegylated formulation of interferon developed as a therapeutic agent of hepatitis; pegylated formulations of glucocerebrosidase and hemoglobin, and so on.

In addition to PEG, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers) are generally used in the chemical coupling of the protein therapeutic agent.

Since the PEG, which is a polymeric compound having a general formula: HO—(—CH$_2$CH$_2$O—)n-H, is highly hydrophilic, it binds with a protein for use in medical applications, thereby increasing the solubility. The PEG binding to the protein has a molecular weight in the range of about 1,000 and about 100,000. If the molecular weight of PEG exceeds 1,000, the PEG has significantly low toxicity. PEGs having a molecular weight in the range of about 1,000 and about 6,000 are present systemically and metabolized through the kidney. In particular, branched PEGs having a molecular weight of about 40,000 are present in organs such as blood, liver, or the like, and metabolized through the kidney.

U.S. Pat. No. 4,179,337 discloses a physiologically active non-immunogenic watersoluble polypeptide composition having polypeptides coupled to polyethylene glycol (PEG) or polypropylene glycol (PPG) having a molecular weight of 500 to 20,000 daltons. In order to couple the PEG to a polypeptide, an activated PEG is generally used. The activated PEG is prepared by converting one end hydroxy group of the PEG into a methyl ether group and the other end hydroxy group into an electrophilic group, thereby coupling the PEG to the polypeptide through the electrophilic group. However, since such a chemical coupling reaction is non-specific, the PEGylated to the active site of the protein, i.e., the polypeptide, undesirably reduces the activity of the protein, an example of which is found from PEGylated interferon-α, developed by Roche and Schering. A PEG conjugate of the interferon-α developed by Roche and Schering is a conjugate in which a molecule of PEG is combined with a molecule of interferon-α. Although the PEG conjugation increased the in vivo half-life of pegylated interferon-α, PEGs are coupled to various sites of interferon-α, thereby considerably reducing the biological activity.

Examples of commonly used activated PEG include (a) PEG dichlorotriazine, (b) PEG tresylate, (c) PEG succinimidyl carbonate, (d) PEG benzotriazole carbonate, (e) PEG p-nitrophenyl carbonate, (f) PEG trichlorophenyl carbonate, (h) PEG succinimidyl succinate, and the like (M. J. Roberts, M. D. Bentley, J. M. Harris, Chemistry for peptide and protein PEG conjugation, Advanced Drug Delivery Reviews 54 (2002) 459-476). Since the chemical coupling reaction is non-specific, a multimer having multiple PEGs boned thereto or an isomer having PEGs bonded to different sites thereof may be produced. The multimer and isomer reduce the biological activity of the PEGylated product, make accurate pharmacokinetic measurement and purification process of the PEG conjugation difficult.

To overcome these problems, U.S. Pat. No. 5,766,897 and WO 00/42175 disclose a method of selectively coupling PEG to cysteine (Cys) residue of protein using PEG-maleimide. A free cysteine that is not associated with disulfide bonding is necessary to couple the PEG to the protein through a cysteine specific PEG conjugation. In the G-CSF containing 5 cysteines, disulfide bonds are formed between cysteines at positions 36 and 42 (based on natural G-CSF) and between cysteines at positions 64 and 74 (based on natural G-CSF), while cysteine at position 17 is a free cysteine. Formation of the two disulfide bonds between cysteine at position 36 and cysteine at position 42 and between cysteine at position 64 and cysteine at position 74 is critically important in the construction of natural G-CSF and maintenance of the biological activity of G-CSF. Since the biological activity of G-CSF is not seriously affected by substitution of cysteine at position 17, cysteine at position 17, with serine, the construction of natural G-CSF and the biological activity of G-CSF are not be attributable to the substitution of cysteine at position 17 with serine (Winfield et al.: Biochem. J. 256, 1988, 213). However, Piget et al. has reported that cysteine at position 17 may form intermolecular disulfide bonds or intramolecular disulfide bonds according to reaction conditions, thereby impeding refolding and lowering the biological activity and stability of G-CSF (Proc. Natl. Acad. Sci. U.S.A., 83, 1986, 7643).

Meanwhile, it has been reported that substitution of cysteine at position 17 of G-CSF, which is the only free cysteine present in G-CSF (Kyowa Hakko, Tokyo, Japan), with serine causes little change in the biological activity of G-CSF (see Korean Patent Registration No. 10-0114369).

One of exemplary therapeutic agents developed using mutant G-CSF is Neu-up® (Component name: Nartograstim) manufactured by Kyowa Hakko, Tokyo, Japan. Reportedly, the mutant G-CSF showed markedly high activity and a longer in vivo half-life compared to natural G-CSF. However, no clinical benefit of the mutant G-CSF has yet been reported.

A pegylated product of N-terminal specific conjugation between G-CSF and PEG, referred to as PEG-G-CSF, was commercially available by Amgen, Inc. (Neulasta®, peg-Filgrastim).

Development of mutant G-CSF for chemical conjugations has been proposed by Maxygen Inc. (PCT/DK2001/00011). According to the proposed publication, however, characteristics of the mutant G-CSF and PEG-G-CSFs produced therefrom are not well described. The mutants can be prepared in various manners. That is to say, there are several thousands to several tens of thousands of possible mutants according to the selection of mutation location, mutation type (insertion, substitution, deletion), mutation extent (1-2 residue~fragment), and combinations thereof, and their biological properties and physiochemical properties for the respective cases would differ. Apparently, chemical conjugates produced from the mutants would differ.

Generally, preparation of mutants for forming chemical bonds is designed based on the knowledge of their structures. According to Osslund et. al. (U.S. Pat. No. 5,581,476), binding sites are selected based on accessible residues, and a binding site that is not interfered from the chemical binding is selected from a structure in which a G-CSF molecule is connected to a G-CSF receptor to restrict the number of target mutants, thereby selecting mutants to be actually subjected to formation of chemical bonds. However, selecting of the mutation position with the knowledge of the structure in such a manner will be easily contemplated by one skilled in the art.

During addition and insertion associated with mutation, the number of residues added and inserted and the character of the mutation (i.e., the type of residues for mutation) considerably affect the biological activity of the mutant. Interchanging a hydrophobic residue and a hydrophilic residue or interchanging a large number of residues and a small number of residues has a substantial effect on the structure of the mutant. One skilled in the art can easily speculate that such structural effect would lead to a considerable change in the biological activity and stability of G-CSF. Particularly, induction of free cysteine to G-CSF exerts a considerable effect on the stability of protein, as proposed by Freeman M L et al. (Destabilization and denaturation of cellular protein by glutathione depletion, Cell Stress Chaperones. 1997 September; 2 (3):191-8).

DISCLOSURE OF INVENTION

Technical Problem

To solve the above problems, it is an objective of the present invention to provide a mutant of a cysteine-inserted human granulocyte-colony stimulating factor (G-CSF), which facilitates specific conjugation with a biocompatible polymer such as polyethylene glycol (PEG) by inserting cysteine to a specific site of G-CSF, increases its in vivo retention time without reducing in vivo biological activity due to the conjugation with the biocompatible polymer, thereby ultimately extending the in vivo biological activity, and a biocompatible conjugated polypeptides thereof.

Technical Solution

The mutant of G-CSF and the chemical conjugate thereof according to the present invention will now be described in greater detail.

In the present invention, naturally occurring G-CSF is expressed by SEQ ID NO:1, and recombinant G-CSF (rG-CSF) is expressed by SEQ ID NO:2. Unless otherwise specified, the term G-CSF used in the present invention encompasses both natural G-CSF and recombinant G-CSF.

To achieve the objective of the present invention, there is provided a mutant of a human granulocyte-colony stimulating factor (G-CSF), the mutant comprising the amino acid sequence identified in SEQ ID NO:3, wherein a threonine (Thr) residue at position 133 of G-CSF comprising the amino acid sequence identified in SEQ ID NO:1, is substituted with a cysteine (Cys) residue.

In addition, the present invention provides a mutant of a G-CSF, wherein a threonine (Thr) residue at position 133 of G-CSF comprising the amino acid sequence identified in SEQ ID NO:1, is substituted with a cysteine (Cys) residue, and a nonprotein chemical compound is modified to the substituted Cys residue.

The present invention also provides a conjugated mutant of a G-CSF comprising the amino acid sequence identified in SEQ ID NO:4, wherein SEQ ID NO:4 has the amino acid sequence that a threonine (Thr) residue at position 133 of G-CSF identified in SEQ ID NO:1 is substituted with a cysteine (Cys) residue, and cysteine (Cys) residue at position 17 in SEQ ID NO:1 is substituted with serine (Ser), and the nonprotein chemical compound is modified to the substituted cysteine residue at position 133.

The nonprotein chemical compound is an activated biocompatible polymer to be chemically conjugated with a thiol group of Cysteine at position 133 and is preferably a compound of one kind selected from the group consisting of polyethylene glycol (PEG), polyvinyl alcohol (PVA), polycarboxylic acid and polyvinyl pyrrolidone, binding with one kind selected from the group consisting of maleimide, vinyl sulfone, iodacetamide and orthopyridyl disulfide. More preferably, the nonprotein chemical compound is a biocompatible polymer of PEG-maleimide.

In addition, the nonprotein chemical compound preferably has a molecular weight in the range of about 2 to about 100 kDa, more preferably in the range of about 5 to about 100 kDa.

In another aspect, there is provided a mutant of a human granulocyte-colony stimulating factor (G-CSF), the mutant comprising the amino acid sequence identified in SEQ ID NO:5, wherein a cysteine (Cys) residue is inserted between a glycine (Gly) residue at position 135 and an alanine (Ala) residue at position 136 of the G-CSF having the amino acid sequence identified in SEQ ID NO:1.

The present invention also provides a conjugated mutant of a G-CSF comprising the amino acid sequence identified in SEQ ID NO:5, wherein a cysteine (Cys) residue is inserted between a glycine (Gly) residue at position 135 and an alanine (Ala) residue at position 136 of the G-CSF having the amino acid sequence identified in SEQ ID NO:1, and a nonprotein chemical compound is modified to the inserted cysteine residue.

The present invention also provides a conjugated mutant of a G-CSF comprising the amino acid sequence identified in SEQ ID NO:6, wherein a cysteine (Cys) residue is inserted between a glycine (Gly) residue at position 135 and an alanine (Ala) residue at position 136 of G-CSF comprising the amino acid sequence identified in SEQ ID NO:1, and a cysteine residue at position 17 is substituted with a serine (Ser) residue, and a nonprotein chemical compound is modified to a inserted cysteine (Cys) residue at position 136.

The nonprotein chemical compound is an activated biocompatible polymer to be chemically conjugated with a thiol group of Cysteine at position 133 and is preferably a compound of one kind selected from the group consisting of polyethylene glycol (PEG), polyvinyl alcohol (PVA), polycarboxylic acid and polyvinyl pyrrolidone, binding with one kind selected from the group consisting of maleimide, vinyl sulfone, iodacetamide and orthopyridyl disulfide. More preferably, the nonprotein chemical compound is a biocompatible polymer of PEG-maleimide.

In addition, the nonprotein chemical compound preferably has a molecular weight in the range of about 2 to about 100 kDa, more preferably in the range of about 5 to about 60 kDa.

The mutant of G-CSF useful in the practice of this invention may be a form isolated from mammalian organisms or, alternatively, a product of chemical synthetic procedures, or of prokaryotic or eukaryotic host expression of exogenous DNA sequences obtained by genomic or cDNA cloning or by DNA synthesis. Suitable prokaryotic hosts include various bacteria (e.g., *E. coli*), suitable eukaryotic hosts include yeast (e.g., *S. cerevisiae*) and mammalian cells (e.g., Chinese hamster ovary cells, monkey cells). Depending upon the host employed, the G-CSF expression product may be glycosylated or non-glycosylated. The G-CSF expression product may also include an initial methionine amino acid residue. The mutant of G-CSF can be produced from transgenic mammalian organisms and can be obtained from milk, blood or urine of cows, sheep, pigs, rabbits, goats, and various species of mammalian animals. To attach PEG to an inserted free cysteine, it is necessary to prepare a mutant of a G-CSF having a free cysteine inserted at a position where the pegylation is easily performed and biological activity is maintained even after the attachment of PEG. To achieve this purpose, inventors of the present invention inserted a free cysteine to a structurally flexible CD-loop region by substitution or insertion, and conjugated PEG to the inserted free cysteine to yield mutant G-CSF. Then, they screened mutants of PEG-G-CSF conjugates maintaining their biological activity and structural stability in the course of pegylation.

In the X-ray diffraction structure of G-CSF(PDB ID, 1bgc), the CD loop region is considered as being considerably flexible and exerting no serious effect on the overall structure of G-CSF. Accordingly, the present inventors prepared mutants having cysteine inserted at the CD loop ($Gly^{126}$-$Ser^{143}$) of rG-CSF identified in SEQ ID NO:2. As seen from several X ray crystalline structures (PDB ID, 1bgc), the CD loop region was expected to be structurally unclear, flexible region, so that a structural change due to pegylation can be dampened. In addition, the inventors could forecast that CD loop region would be an area in which polymeric materials are easily accessible because it had sufficient external sites for chemical modifications. Further, the CD loop region had a receptor binding structure without a region overlapping with a receptor, which is advantageous for forming chemical bonds.

In such a manner, the inventors of the present invention prepared mutants having cysteine inserted to the CD loop region (126-Gly Met Ala Pro Ala Leu Gln Pro Thr Gln Gly Ala Met Pro Ala Phe Ala Ser-143: SEQ ID NO:2) and then screened mutants of PEG-G-CSF conjugates during pegylation. The resultant cysteine inserted mutants showed considerable differences in the stability and PEG conjugation performance according to the induction position. Some mutants showed high stability and high levels in expression and purification efficiency while exhibiting poor PEG conjugation performance, suggesting that the PEG conjugation is not readily performed under the microenvironment around which mutations occur due to steric hindrance or effect of nearby residues. In addition, some mutants having instability were quite difficult to express and purify, resulting in formation of precipitates in a purification step.

One of merits expected by PEG conjugation of cysteine-inserted mutant G-CSF is accuracy of PEG conjugation. The PEG conjugation to lysine or N-terminal amine of a protein is carried out through (a) PEG dichlorotriazine, (b) PEG tresylate, (c) PEG succinimidyl carbonate, (d) PEG benzotriazole carbonate, (e) PEG p-nitrophenyl carbonate, (f) PEG trichlorophenyl carbonate, (g) PEG carbonylimidazole, and (h) PEG succinimidyl succinate. The above PEG conjugation is non-specific and double or more equivalents PEGs are conjugated to lysine or N-terminal amine of the protein. Even though the same equivalent PEGs are conjugated, regional isomers are produced which are conjugated to the random position. Then, these procedures increase the time and cost to delete the produced conjugates (M. J. Roberts et al., Chemistry for peptide and protein PEG conjugation, Advanced Drug Delivery Reviews 54 (2002), 459-476). Another merit of PEG conjugation is to optionally select PEG attachment sites. The PEG attachment sites are comprehensive, inclusive of Lysine, Aspatate, Glutamate, Alpha-amine, carboxyl, and so on. Accordingly, if a PEG attachment site is structurally important portion affecting the activity, PEG conjugation may significantly degrade the activity. From this viewpoint, specific pegylation by cysteine insertion would be advantageously used in development of PEG conjugates for maintaining the biological activity.

Since a free thiol group is highly reactive, it is readily oxidized (Rigo A et al., Interaction of copper with cysteine: stability of cuprous complexes and catalytic role of cupric ions in anaerobic thiol oxidation, J Inorg Biochem. 2004, 98(9), 1495-501). However, in some case, free thiol residues may form disulfide bonds. In order to cause chemical modification, free thiol groups induced to a protein surface may form intermolecular disulfide bonds, which results in secondary sedimentation or oxidation, thereby disabling chemical modification (Crow M K, et. al., Protein aggregation mediated by cysteine oxidation during the stacking phase of discontinuous buffer SDS-PAGE, Biotechniques 2001, 30(2), 311-6). Such undesirable phenomenon becomes severe when the sites of inserted cysteine residues are exposed outside. Thus, selecting of cysteine-insertion sites for specific chemical modification based on only the knowledge of the structure may encounter severe problems, e.g., protein instability due to free cysteine (Grzegorz Bulaj, Formation of disulfide bonds in proteins and peptides, Biotechnology Advances 23 (2005) 87-92).

Most of cysteine-inserted mutant G-CSF prepared in the present invention demonstrated low expression and purification efficiency. To solve the instability problem of protein having free cysteine residues, COX G. N. et al. employed methods specially devised for overcoming the instability problem to preparation of cysteine-inserted mutants, as described in WO 00/42175. Although such attempted methods rather mitigated intrinsic instability of free cysteine inserted mutants, they are quite difficult to be applied to practical production processes. For example, as described in WO 00/42175, intracellular expression of a protein is advantageous in achieving the stability of a cysteine inserted mutant. However, to purify a cysteine inserted mutant, the cysteine inserted mutant should be secreted into an extracellular space. The principle of the invention described in WO 00/42175 lies in that the extracellular stability is maintained by keeping the redox potential level constant using a redox coupling agent, etc. However, it is quite difficult to keep the redox potential at a constant level over an extended period of time, particularly during a purification step. However, in the present invention, cysteine-inserted mutants compatible with general folding and purification steps were selectively prepared, confirming that the cysteine-inserted mutants according to the present invention maintain structural stability even if they have free cysteine residues. The cysteine-inserted mutant G-CSF selected in the present invention are expressed in E. coli. as inclusion bodies and transformed into active mutant G-CSF by general refolding technique. The general refolding technique is accomplished by solubilizing an inclusion body in urea or guanidium salt and removing the urea or guanidium salt by dilution or deletion to provide for the biological activity. According to the presence or absence of disulfide bonds in the protein, a redox-coupling agent (either oxidized or reduced form of glutatione or cysteine) may be added to the refolding step (Ronald W et al., Disulphide bond formation in food protein aggregation and gelation, Biotechnology Advances 23 (2005) 75-80). In the present invention, refolding was performed in the following manner. That is, the inclusion body of cysteine inserted mutant G-CSF was preferably dissolved in 6-8 M urea and diluted in 2-4 M urea in the presence of glutathione to refold them.

The PEG polymer used for conjugation has no particular limitation on a molecular weight but preferably has a molecular weight in the range of about 2 kDa to 100 kDa, more preferably in the range of about 10 kDa to 60 kDa. A method of coupling PEG-maleimide as a biocompatible polymer to an inserted cysteine-thiol residue of cysteine-inserted G-CSF is used in the present invention. That is to say, G-CSF was reacted with 20 kDa or 30 kDa PEG-maleimide to prepare 20 kDa or 30 kDa PEG-G-CSF conjugate.

In the PEG conjugation reaction of biocompatible polymer to the thiol residue of cysteine-inserted G-CSF, the molar ratio of PEG to G-CSF was preferably in the ratio of 2:1 to 200:1, and the reaction temperature was preferably in the range of about 0 to about 60□. The reaction was preferably carried out at a pH of about 5.0 to about 7.7, and the reaction time was preferably in the range of about 5 minutes to about 24 hours.

After performing the pegylation in the method described in the present invention, conjugation between PEG and mutant G-CSF was identified by SDS-PAGE analysis. To obtain mono-PEG-G-CSF conjugates from conjugated reactants, mono-PEG-G-CSF derivatives were isolated using cation exchange chromatography. The derivatives isolated using the cation exchange chromatography were further subjected to size exclusion chromatography to isolate only mono-PEG-G-CSF conjugates that is removed with a trivial amount of unreacted G-CSF.

To measure the biological activity of mono-PEG-G-CSF derivatives of the present invention, known methods described in various documents (Baldwin et al., Acta Endocrinologica., 119:326, 1988; Clark et al., J. Biol. Chem., 271(36):21969, 1996; and Bozzola et al., J. endocrinol. Invest., 21:768, 1998) were used. The measurement results demonstrated that the PEG-G-CSF conjugates according to the present invention had an increased in vivo retention time while maintaining a high level of biological activity.

The N-terminally monopegylated Filgrastim reportedly had 68% of the in vitro biological activity of Filgrastim. (U.S. Pat. No. 5,824,784). By contrast, each of the PEG-G-CSF conjugates according to the present invention had about 2.1 to about 3.5 times the in vitro biological activity (that is, 250-300%) of Filgrastim. In addition, the in vivo half-life of each of the PEG-G-CSF conjugates according to the present invention was at least about 5 times that of the Filgrastim. Further, it was superior to the Filgrastim in the neutrophil activation bioactivity. The reasons of the foregoing are presumably as follows. That is, the bioactivity and stability of G-CSF are not affected by the selected position of inserted cysteine and the selected position is a position at which a structural change due to pegylation of G-CSF can be flexibly dampened.

Advantageous Effects

As described above, the present invention can provide for a mutant of a cysteine-inserted granulocyte-colony stimulating factor (G-CSF), which facilitates specific conjugation with a biocompatible polymer such as polyethylene glycol (PEG) by inducing cysteine to a specific site of G-CSF, increases its in-vivo retention time without reducing in-vivo biological activity due to the conjugation with the biocompatible polymer, thereby ultimately extending the in-vivo biological activity, and a biocompatible conjugated polypeptides thereof. In addition, since the PEG-G-CSF conjugates according to the present invention had higher plasma stability than Filgrastim in view of pharmacokinetics profile, 4.2-5.1 times longer in vivo half-life, thereby maintaining the activity and extended therapeutic effect. Further, the neutrophil activation effect are superior to the Filgrastim in the pharmacodynamics.

BEST MODE FOR CARRYING OUT THE INVENTION

Figure 1:
FIG. 1 is a schematic diagram of a PEG-G-CSF conjugation reaction

Hereinafter, the present invention will be described in greater detail with reference to the following examples. The following examples are offered to illustrate, but not to limit the present invention.

Examples 1~11

Preparation of Conjugated Mutant G-CSF by Cysteine Substitution of Amino Acids in CD Loop (Glyl$^{26}$-Ser$^{143}$) of G-CSF Identified in SEQ ID NO:2

A. Preparation of Recombinant G-CSF (rG-CSF)

The recombinant G-CSF (rG-CSF) used in the present invention was expressed using the strain (KFCC-10961) described in Korean Patent No. 230579 to the applicant of the present invention. The thus prepared recombinant G-CSF, which is derived from E. coli, like Filgrastim, has the amino acid sequence identified in SEQ ID NO:2. In these Examples, based on the fact that a recombinant G-CSF is used as a G-CSF, the prepared recombinant G-CSF is assigned a amino acid sequence number on the basis of the amino acid sequence identified in SEQ ID NO:2.

B. Preparation of Cysteine-Inserted Mutants of Recombinant G-CSF

Cysteine-inserted mutant G-CSF was prepared from the G-CSF expression strain (KFCC-10961) described in Korean Patent No. 230579. The G-CSF expression strain was cultured in an LB culture medium with agitation for 12 hours and then isolated a G-CSF expression vector (pGW2) using a plasmid preparation kit manufactured by Quiagen, Inc. A polymerase chain reaction (PCR) was performed on the isolated G-CSF expression vector (pGW2) as a template using complementary mutation primers containing a cysteine-inserted gene (complementary polynucleotide double-strand having a length of 30-40 base pairs) listed in Table 1. The resultant G-CSF expression vector cloned with PCR was then treated with a DPN 1 enzyme that removes the template, to then be transformed to rubidium-treated MC 1061 E. coli. The transformed host was cultured in an Ampicilin culture medium for screening transformant strains. The enzymatic treatment of PCR for mutation and template removal was performed using pfuTurbo DNA polymerase and DPN 1 enzyme which are available from the site-directed mutagenesis kit (QuikChange Site-Directed Mutagenesis Kit, Stratagen, Inc.), respectively, in accordance with user guidelines. Mutation was confirmed by analysis of base sequencing through PCR using a primer (5'-GCGGATCCTGCCTGA-3').

C. Expression of Cysteine-Inserted Mutant G-CSF

Cysteine-inserted mutant G-CSF was cultured in 5 ml LB culture media each supplemented with 5 µg/ml Ampicilin for 12 hours to then be transferred to 500 ml LB media supplemented with 5 µg/ml Ampicilin for culturing with agitation. When the optical density (OD) of the strain reached 0.5, a final concentration 1% (w/v) of arabinose was added to the respective culture media and cultured with agitation for about 7 hours, to thus overexpress the cysteine-inserted mutant G-CSF.

D. Refolding of Cysteine-Inserted Mutant G-CSF

Strains of the overexpressed cysteine-inserted mutant G-CSF were centrifuged to be suspended in Tris 20 mM and 150 mM NaCl, and the suspended strains were disrupted using a sonicator. The disrupted strains were centrifuged and washed with 2% (w/v) sodium deoxycholate to recover inclusion bodies. The inclusion bodies of the cysteine-inserted mutants were dissolved in 7 M urea, 20 mM Tris, and 100 mM NaCl at pH 8.8, and 10-fold diluted in 3.3 M urea, 5 mM Tris, 2 mM reduced glutathione, and 0.2 M oxidized glutathione at pH 8.8. The refolding step was performed with agitation at 4☐ for 18 hours.

E-1. Preparation of Peqylated Cysteine-Inserted Mutant G-CSF

After titration of a cysteine-inserted mutant G-CSF as a refolding sample with HCl to reach pH 4.5, the resultant precipitate was removed by centrifuging. To purify the cysteine-inserted mutant G-CSF having activity, 20 mM sodium phosphate was injected into a SP-sepharos fast flow column equilibrated at pH 4.0, washed using an equilibration buffer, eluted with a gradient of salt concentrations 100-5000 mM NaCl. The pH of the eluted cysteine-inserted mutant G-CSF sample was adjusted to 6.8, and methoxy-PEG-maleimide having an average molecular weight of about 20 kDa or about 30 kDa (Shearwater, Inc, U.S.A.) was added to the resultant solution so that the molar ratio of cysteine-inserted mutant G-CSF:methoxy-PEG-maleimide becomes 1:2. Then, the reaction was allowed to occur at 4☐ for about 18 hours with slow agitation.

E-2. Preparation of Vinyl Sulfone-Pegylated Cysteine-Inserted Mutant G-CSF

After adjusting the pH of the SP-sepharos effluent sample of the cysteine inserted mutant G-CSF isolated by the same method as described in section E-1 to pH 7.5, methoxy-PEGvinylsulfone having an average molecular weight of about 20 kDa was added to the resultant solution so that the molar ratio of cysteine-inserted mutant G-CSF:methoxy-PEG-maleimide becomes 1:5. Then, the reaction was allowed to occur at 4□ for about 18 hours with slow agitation.

E-3. Preparation of Iodoacetimide-Pegylated Cysteine-Inserted Mutant G-CSF

After adjusting the pH of the SP-sepharos effluent sample of the cysteine inserted mutant G-CSF isolated by the same method as described in section E-1 to pH 7.0, methoxy-PEG-iodoacetimide having an average molecular weight of about 20 kDa was added to the resultant solution so that the molar ratio of cysteine-inserted mutant G-CSF:methoxy-PEG-iodoacetimide becomes 1:2. Then, the reaction was allowed to occur in a dark room at 4□ for about 48 hours with slow agitation.

F. Isolation of Fused Body of Mono-PEG-G-CSF Derivative

After adjusting the pH of the prepared pegylated cysteine-inserted mutant G-CSF to pH 4.0, the resultant product was 3-fold diluted in a buffer solution (20 mM $Na_2HPO_4$ mono basic, pH 4.8), and injected into a SP-sepharos fast flow column equilibrated using a equilibration buffer equilibration buffer same buffer, that is, an equilibration buffer containing a 20 mM $Na_2HPO_4$ mono basic, pH 4.8. Then, the resultant product was washed with a buffer solution (20 mM $Na_2HPO_4$ mono basic, 50 mM NaCl, pH 4.8) and then eluted with a gradient of salt concentrations 50-500 mM NaCl. To remove unreacted G-CSF from the cysteine-inserted mutant G-CSF, size exclusion chromatography was performed on the pegylated cysteine-inserted mutant G-CSF eluted from the SP-sepharose column. The SP-sepharose effluent was concentrated and injected into Superdex 200 (2.5×50 cm, Pharmacia) equilibrated with a buffer solution (20 mM $Na_2HPO_4$ mono basic, 100 mM NaCl (pH4.0)) and eluted with the same buffer solution at an elution rate of 1 ml/min. The purity of the isolated pegylated cysteine-inserted mutant G-CSF was determined by SDS-PAGE analysis.

Table 1 demonstrates the recovery and conjugation performance of each of the pegylated cysteine-inserted mutants prepared in Examples 1 through 11 indicated in percentile (%).

TABLE 1

| | Mutant | | |
|---|---|---|---|
| Example | Mutation site | Mutant Recovery (%) | Maleimide-PEG Conjugation Performance (%) |
| 1 | Ala 128 Cys | 0.01 | 0 |
| 2 | Ala 130 Cys | 8 | 3 |
| 3 | Leu 131 Cys | 30 | 3 |
| 4 | Gln 132 Cys | 50 | 35 |
| 5 | Thr 134 Cys | 50 | 70 |
| 6 | Gln 135 Cys | 40 | 70 |
| 7 | Gly 136 Cys | 18 | 0.01 |
| 8 | Ala 137 Cys | 62 | 30 |
| 9 | Met 138 Cys | 34 | 0.01 |
| 10 | Ala 140 Cys | 0.01 | 0 |
| 11 | Ala 142 Cys | 0.01 | 0 |

[In Tables of the present invention, the notation indicated in the column of mutation site, e.g., "Ala 128 Cys", means that the amino acid numbered 128, that is, Ala, is substituted with Cys, and the notation is applied with other examples in same manner]

[Mutant recovery means the yield of mutants through refolding and purification performed for PEG-mutant conjugation, that is, the proportion of a number of purified mutant G-CSF to overall counts of mutant G-CSF expressed in inclusion bodies.]

[PEG conjugation performance means a proportion of a number of G-CSFs conjugated to PEG to a total number of mutant G-CSF associated with PEG conjugation.]

Examples 12~22

Preparation of Conjugated Mutant G-CSF Conjugates by Substitution of Cysteines in Amino Acids of G-CSF in CD Loop ($Gly^{126}$-$Ser^{143}$) and Serine Substitution of Cysteine at Position 18

The subject mutants were prepared in the same manners as in Examples 1 through 11, except that in order to prepare mutants by embracing both substitutions of cysteines (Cys) in amino acids with serines and a substitution of cysteine at position 18 with serine in a CD loop ($Gly^{126}$-$Ser^{143}$), cysteine-inserted mutation was performed using Cys 18 Ser substituted mutant strains and the cysteine-inserted mutation was performed in the same manner as described above. The present inventors prepared mutants having cysteine-inserted-cysteine insertedat the CD loop of rG-CSF identified in SEQ ID NO:2.

Table 2 demonstrates the recovery and conjugation performance of each of the pegylated cysteine-inserted mutants prepared in Examples 12 through 22 indicated in percentile (%).

TABLE 2

| | Mutant | | |
|---|---|---|---|
| Example | Mutation site | Mutant Recovery(%) | Maleimide-PEG conjugation (%) |
| 12 | Ala 128 Cys, Cys 18 Ser | 0.5 | 0 |
| 13 | Ala 130 Cys, Cys 18 Ser | 10 | 10 |
| 14 | Leu 131 Cys, Cys 18 Ser | 30 | 5 |
| 15 | Gln 132 Cys, Cys 18 Ser | 45 | 30 |
| 16 | Thr 134 Cys, Cys 18 Ser | 55 | 75 |
| 17 | Gln 135 Cys, Cys 18 Ser | 43 | 65 |
| 18 | Gly 136 Cys, Cys 18 Ser | 15 | 0.01 |
| 19 | Ala 137 Cys, Cys 18 Ser | 64 | 35 |
| 20 | Met 138 Cys, Cys 18 Ser | 30 | 0.01 |
| 21 | Ala 140 Cys, Cys 18 Ser | 0.01 | 0 |
| 22 | Ala 142 Cys, Cys 18 Ser | 0.01 | 0 |

Examples 23~28

Preparation of Mutants of G-CSF Conjugates by Insertion of Cysteines (Cys) in CD Loop ($Gly^{126}$-$Ser^{143}$) of G-CSF The subject mutants were prepared in the same manners as in Examples 1 through 11, except that in order to prepare mutants by insertion of cysteine (Cys) into a CD loop ($Gly^{126}$-$Ser^{143}$), a polymerase chain reaction (PCR) was performed on the isolated G-CSF expression vector (pGW2) as a template using complementary mutation primers containing a cysteine-inserted gene (complementary polynucleotide double-strand having a length of 30-40 base pairs) listed in Table 3.

Table 3 demonstrates the recovery and conjugation performance of each of the pegylated cysteine-inserted mutants prepared in Examples 23 through 28 indicated in percentile (%).

TABLE 3

| Example | Mutation site | Mutant Recovery (%) | Maleimide-PEG conjugation (%) |
|---|---|---|---|
| 23 | 130 Cys 131 | 45 | 45 |
| 24 | 131 Cys 132 | 40 | 20 |
| 25 | 134 Cys 135 | 45 | 0.01 |
| 26 | 135 Cys 136 | 50 | 37 |
| 27 | 136 Cys 137 | 75 | 85 |
| 28 | 137 Cys 138 | 25 | 15 |

[In Tables of the present invention, the notation indicated in the column of mutation site, e.g., "130 Cys 131", means that the amino acid Cys is inserted between amino acids numbered 130 and 131, and the notation is applied with other examples in same manner]

Examples 29~34

Preparation of Mutants of G-CSF Conjugates by Insertion of Cysteines (Cys) in CD Loop ($Gly^{126}$-$Ser^{143}$) of G-CSF and Serine Substitution of Cysteine at Position 18

The subject mutants were prepared in the same manners as in Examples 23 through 28, except that in order to prepare mutants by embracing both insertion of cysteines (Cys) in amino acids and a substitution of cysteine at position 18 with serine in a CD loop ($Gly^{126}$-$Ser^{143}$), cysteine-inserted mutation was performed using Cys 18 Ser substituted mutant strains and the cysteine-inserted mutation was performed in the same manner as described above.

Table 4 demonstrates the recovery and conjugation performance of each of the pegylated cysteine-inserted mutants prepared in Examples 29 through 34 indicated in percentile (%).

TABLE 4

| Example | Mutation site | Mutant Recovery (%) | Maleimide-PEG conjugation (%) |
|---|---|---|---|
| 29 | 130 Cys 131, Cys 18 Ser | 50 | 40 |
| 30 | 131 Cys 132, Cys 18 Ser | 45 | 15 |
| 31 | 134 Cys 135, Cys 18 Ser | 55 | 0.01 |
| 32 | 135 Cys 136, Cys 18 Ser | 40 | 43 |
| 33 | 136 Cys 137, Cys 18 Ser | 85 | 70 |
| 34 | 137 Cys 138, Cys 18 Ser | 23 | 20 |

Figure 2:
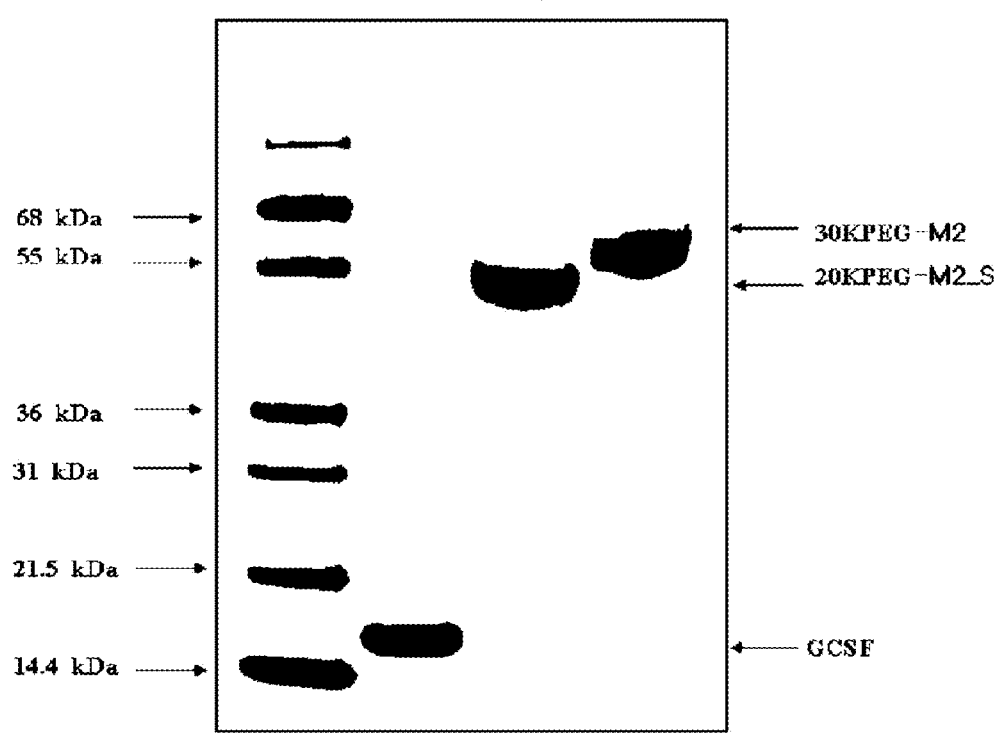
FIG. 2 shows the result of SDS PAGE (sodium dodecyl sulfate-polyacrylamide gel electrophoresis) analysis of a purified mutant of G-CSF and PEG conjugate according to the present invention.

FIG. 2 shows the result of SDS PAGE analysis of a purified PEG conjugate of mutant G-CSF prepared in Example 33 (M2_S) in which Cys 18 is substituted with Ser and Cys is inserted between Gly at position 136 and Ala 137, the purified PEG conjugate obtained by conjugating to 20 kDa PEG-maleimide or 30 kDa PEG-maleimide and purifying the same, showing a single band.

Figure 3:
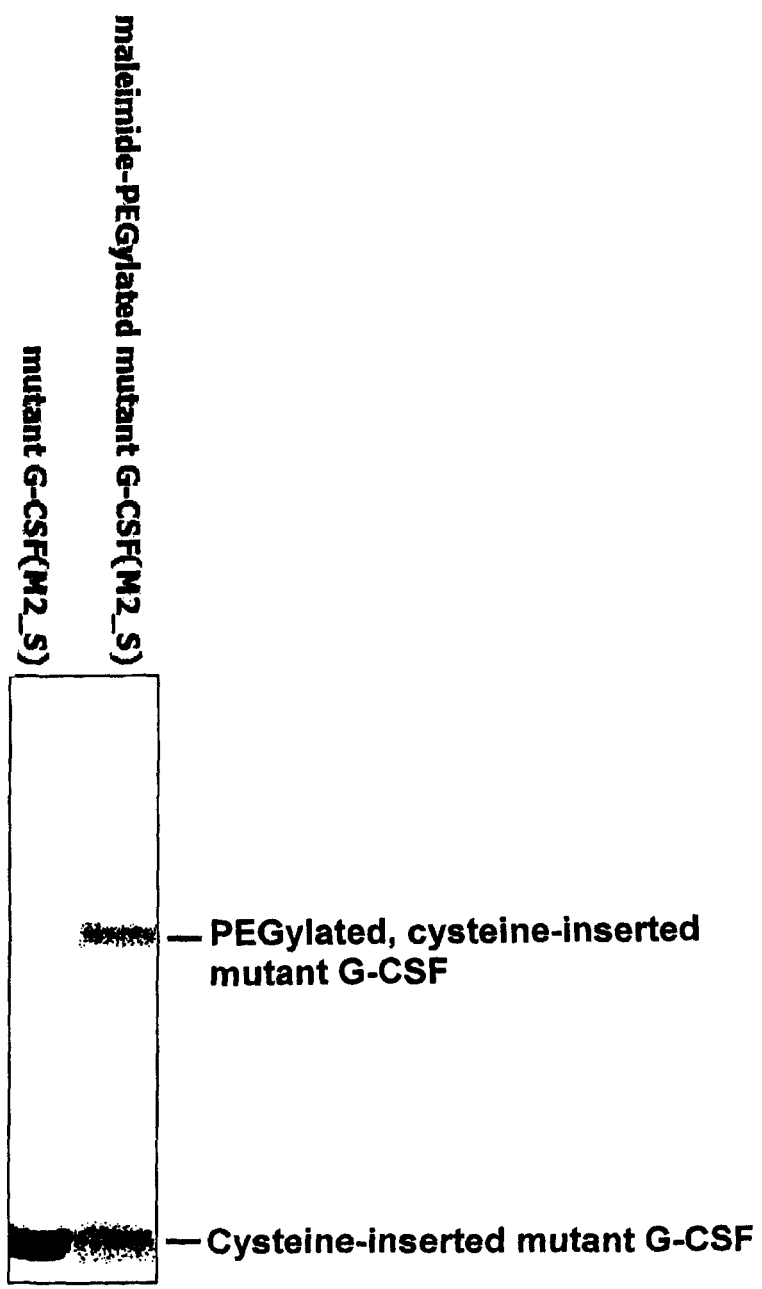
FIG. 3 shows the result of SDS PAGE analysis of G-CSF-PEG conjugation reactants according to the present invention.

FIG. 3 shows the result of SDS PAGE analysis of a 20 kDa PEG conjugate of mutant G-CSF prepared in Example 33 (M2_S) in which Cys 18 is substituted with Ser and Cys is inserted between Gly at position 136 and Ala 137.

As shown in FIG. 3, since the PEG-maleimide conjugation reaction of the cysteine-insertedmutant G-CSF is non-specific to inserted cysteine, a mono-PEG-G-CSF could be obtained without formation of oligomer or polygomer.

Experimental Example 1

Measurement of In Vitro Activity

Biological activities of cysteine-inserted mutant G-CSF PEG conjugates prepared in Examples 1 through 34 were measured and compared with the activity of the Filgrastim (*E. coli* derived G-CSF). The activity measurement was performed through cell proliferation of the murine myeloid leukemic cell line NFS-60 (ATCC X65622). NFS-60 cells are cultured in an RPMI1640 medium containing 10% (v/v) FBS (fetal bovine serum) and a 5% WEHI-1640 cell line medium solution, and suspended in an RPMI medium containing 10% (v/v) FBS to reach a concentration of about $2 \times 10^5$ cells/ml. Each 50 µl of the suspended cell suspension was added to each well of 96 well microtiter plates, each well containing about $1 \times 10^4$ cells.

Filgrastim and PEG conjugates of cysteine-inserted mutants prepared in Examples were diluted in an RPMI 1640 medium containing 10% (v/v) FBS to reach 15 ng/ml using BCA (Bicinconinic acid) protein assay. 3-fold dilution is further performed in an RPMI 1640 medium containing 10% (v/v) FBS in 12 stages. Each 100 µl of the thus prepared samples was added to the respective wells where NFS-60 cells are cultured, so that concentrations of the samples in the culture medium continuously diminished until the final sample concentration reached a range of 10000 to 0.05 pg/ml. After incubating in an incubator at 37□ for 48 hours, proliferation of the cells was confirmed using a CellTiter96™ (Cat. No. G3580) (PROMEGA).

Table 5 demonstrates the overall data of the recovery and conjugation performance of the pegylated cysteine-inserted mutants prepared in Examples 1 through 34.

The mutant recovery indicates the yield of a number of purified mutant G-CSFs from inclusion bodies to a total number of mutant G-CSFs. It is determined that a mutant having relatively high recovery leads to a cysteine-inserted mutant having relatively high stability. Meanwhile, PEG conjugation performance indicates a proportion of a number of G-CSFs conjugated to PEG to a total number of mutant G-CSFs associated with PEG conjugation. Higher PEG performance means that to PEG can be easily coupled to inserted cysteine. The NFS60 activity indicates the in vitro biological activity of a PEG conjugate assuming that the in vitro biological activity of Filgrastim is 100%.

TABLE 5

| | Mutant | | |
|---|---|---|---|
| Example | Mutation site | Mutant Recovery(%) | Maleimide-PEG conjugation (%) | NFS 60 activity of PEG conjugate (%)[based on Filgrastim 100%] |
|---|---|---|---|---|
| 1 | Ala 128 Cys | 0.01 | 0 | — |
| 2 | Ala 130 Cys | 8 | 3 | 21 |
| 3 | Leu 131 Cys | 30 | 3 | 2 |
| 4 | Gln 132 Cys | 50 | 35 | 40 |
| 5 | Thr 134 Cys | 50 | 70 | 210 |
| 6 | Gln 135 Cys | 40 | 70 | 30 |
| 7 | Gly 136 Cys | 18 | 0.01 | — |

TABLE 5-continued

| | | Mutant | | |
|---|---|---|---|---|
| Example | Mutation site | Mutant Recovery(%) | Maleimide-PEG conjugation (%) | NFS 60 activity of PEG conjugate (%)[based on Filgrastim 100%] |
| 8 | Ala 137 Cys | 62 | 30 | 40 |
| 9 | Met 138 Cys | 34 | 0.01 | — |
| 10 | Ala 140 Cys | 0.01 | 0 | — |
| 11 | Ala 142 Cys | 0.01 | 0 | — |
| 12 | Ala 128 Cys, Cys 18 Ser | 0.5 | 0 | — |
| 13 | Ala 130 Cys, Cys 18 Ser | 10 | 10 | 21 |
| 14 | Leu 131 Cys, Cys 18 Ser | 30 | 5 | 5 |
| 15 | Gln 132 Cys, Cys 18 Ser | 45 | 30 | 45 |
| 16 | Thr 134 Cys, Cys 18 Ser | 55 | 75 | 230 |
| 17 | Gln 135 Cys, Cys 18 Ser | 43 | 65 | 45 |
| 18 | Gly 136 Cys, Cys 18 Ser | 15 | 0.01 | — |
| 19 | Ala 137 Cys, Cys 18 Ser | 64 | 35 | 55 |
| 20 | Met 138 Cys, Cys 18 Ser | 30 | 0.01 | — |
| 21 | Ala 140 Cys, Cys 18 Ser | 0.01 | 0 | — |
| 22 | Ala 142 Cys, Cys 18 Ser | 0.01 | 0 | — |
| 23 | 130 Cys 131 | 45 | 45 | 48 |
| 24 | 131 Cys 132 | 40 | 20 | 60 |
| 25 | 134 Cys 135 | 45 | 0.01 | — |
| 26 | 135 Cys 136 | 50 | 37 | 43 |
| 27 | 136 Cys 137 | 75 | 85 | 270 |
| 28 | 137 Cys 138 | 25 | 15 | 65 |
| 29 | 130 Cys 131, Cys 18 Ser | 50 | 40 | 60 |
| 30 | 131 Cys 132, Cys 18 Ser | 45 | 15 | 70 |
| 31 | 134 Cys 135, Cys 18 Ser | 55 | 0.01 | — |
| 32 | 135 Cys 136, Cys 18 Ser | 40 | 43 | 50 |
| 33 | 136 Cys 137, Cys 18 Ser | 85 | 70 | 350 |
| 34 | 137 Cys 138, Cys 18 Ser | 23 | 20 | 70 |

As shown in Table 1, the cysteine-inserted mutants prepared in Example 1, 10, 11, 12, 21 and 22 were not easily expressed and purified. Among cysteine-inserted mutants easily where are expressed and purified, the biological activity of the mutant in which Cys18 is substituted with serine was not considerably different from that of the mutant maintaining cysteine at position 18 without a change. However, the cysteine-inserted mutant maintaining cysteine at position 18 experienced a slight reduction in the biological activity after pegylation. This finding is consistent with the report by Park et al. (Korea Patent Application No. 10-2003-0017606). It is believed that PEG conjugation was performed on cysteine at position 18.

After the screening step, to effect PEG conjugation, i.e., pegylation, a final screening step was performed to determine a mutant G-CSF (M1) in which Thr 134 of G-CSF is substituted with cysteine, a mutant G-CSF (M2) in which Cys is inserted between Gly 136 and Ala 137, mutant G-CSF (M1_S) in which Cys at position 18 is substitute with Ser, and a mutant G-CSF (M2_S) in which Cys at position18 is substitute with Ser and Cys is inserted between Gly 136 and Ala 137. The pegylated M1, M1_S, M2, and M2_S mutants were named 20 kDa PEG-M1, 20 kDa PEG-M1_S, 20 kDa PEG-M2, and 20 kDa PEG-M2_S, respectively.

Experimental Example 2

Measurement of Pharmacokinetics

The serum retention time of each of the 20 kDa PEG conjugated cysteine-inserted mutant G-CSF determined in Experimental Example 1, that is, 20 kDa PEG-M1, kDa PEG-M1_S, 20 kDa PEG-M2 and 20 kDa PEG-M2_S was measured. For each group, Filgrastim (Control) and 20 kDa PEG-M1, 20 kDa PEG-MtS, 20 kDa PEG-M2, and 20 kDa PEG-M2_S prepared in Examples were subcutaneously injected to each 5 SD rats (Male Sprague Dawly Rats, 6 weeks old, weighing 200-250 g) by 100 µg per kg body weight, and blood samples were collected at 0.5, 1, 2, 4, 8, 12, 16, 20, 24, 30, 36, 48, 60, 72, 96, 120, 144 and 168 hours after the injection. The blood samples were coagulated at temperature at room temperature for one hour, followed by centrifuging for 5 minutes at 10000 rpm using a micro-centrifuge, thereby removing cells. A quantity of plasma G-CSF was measured by enzyme-linked immunoadsorption assay (ELISA) using a monoclonal antibody.

Table 6 demonstrates the plasma half lives of test group and proof group.

TABLE 6

| | Control Filgrastim | Example 20 kDa PEG-M1 | Example 20 kDa PEG-M1_S | Example 20 kDa PEG-M2 | Example 20 kDa PEG-M2_S |
|---|---|---|---|---|---|
| Plasma half-life($T_{1/2}$, hr) | 1.9 | 7.9 | 8.2 | 8.9 | 9.7 |

Figure 4:
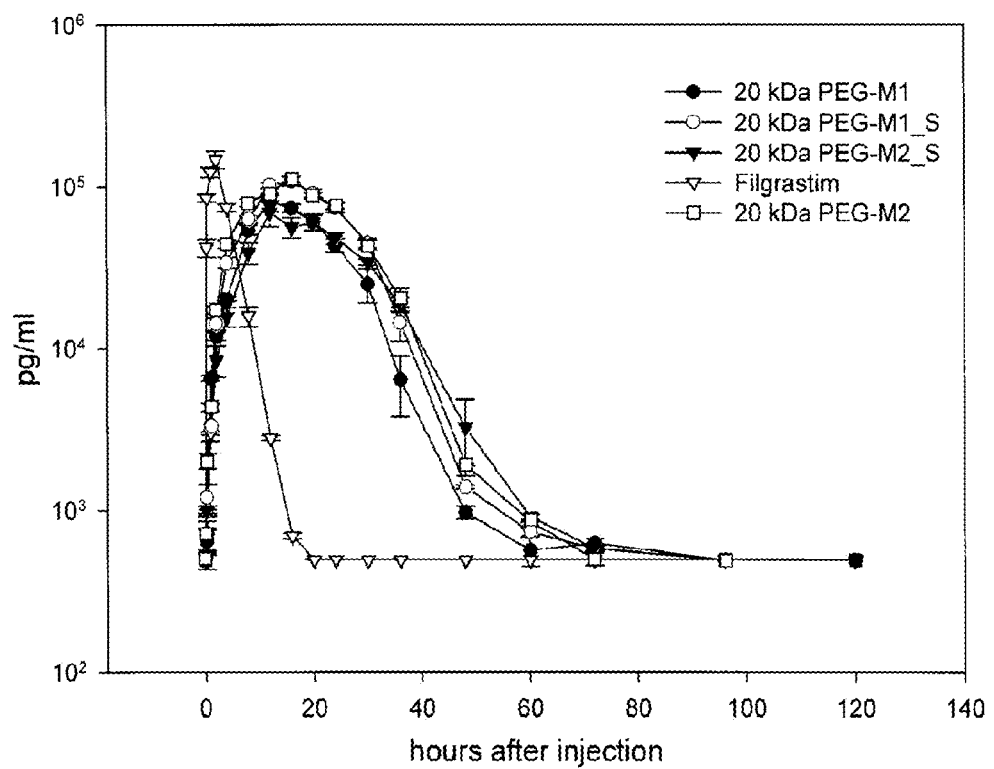
FIG. 4 shows the measurement result of in vivo pharmacokinetics of G-CSF-PEG conjugates according to the present invention.

FIG. 4 shows the measurement result of in vivo pharmacokinetics of G-CSF-PEG conjugates according to the present invention.

Referring to Table 6 and FIG. 4, the 20 kDa of the present invention showed higher plasma stability than Filgrastim, that is, 4.2-5.1 times a longer in vivo half-life than Filgrastim, suggesting that of 20 kDa PEG conjugates of cysteine-inserted mutant G-CSF according to the present invention maintained the in vivo activity for a longer period than Filgrastim, thereby improving the therapeutic efficacy.

Experimental Example 3

Measurement of Drug Pharmacodynamics

The neutrophilactivity of each of the 20 kDa PEG conjugated cysteine-inserted mutant G-CSF determined in Experimental Example 1, that is, 20 kDa PEG-M1, 20 kDa PEG-M1_S, 20 kDa PEG-M2 and 20 kDa PEG-M2_S was measured. For each group, Filgrastim (Control) and 20 kDa PEG-M1, 20 kDa PEG-M1_S, 20 kDa PEG-M2, and 20 kDa PEG-M2_S prepared in Examples were subcutaneously injected to each 5 SD rats (Male Sprague Dawly Rats, 6 weeks old, weighing 200-250 g) by 100 μg per kg body weight, and blood samples were collected by eye-bleeding overtime. Then, the number of plasma neutrophils was counted.

Figure 5:
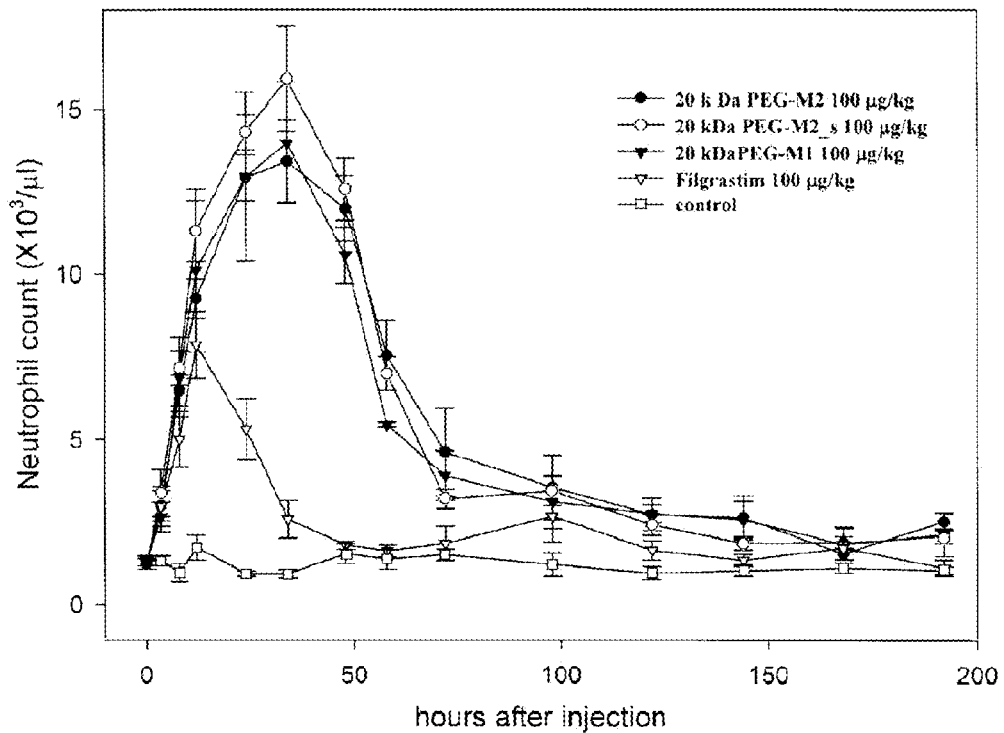
FIG. 5 is a graphical representation illustrating the measurement result of pharmacokinetics for comparing the in vivo activity of neutrophil activation between G-CSF-PEG conjugates.

FIG. 5 is a graphical representation illustrating the measurement result of pharmacokinetics for comparing the in vivo activity of neutrophils between G-CSF-PEG conjugates.

As shown in FIG. 5, the neutrophil activity of each of the 20 kDa PEG conjugated cysteine-inserted mutant G-CSF, that is, 20 kDa PEG-M1, 20 kDa PEG-M1_S, 20 kDa PEG-M2 and 20 kDa PEG-M2_S was much higher than that of the Filgrastim.

INDUSTRIAL APPLICABILITY

As described above, the present invention is directed to a mutant of human granulocyte-colony stimulating factor (G-CSF) as an adjuvant in the treatment of cancer for inhibiting the leukocytopenia by stimulating the formation of neutrophilic granulocyte colonies from bone marrow cells when an anticancer drug is administered, and inducing the differentiation of thebone marrow cells to final phases, and chemically conjugated polypeptides thereof. Accordingly, the present invention is advantageously applicable to medical purposes and treatment of diseases.

The invention claimed is:

1. A mutant of an isolated human granulocyte-colony stimulating factor (G-CSF), the mutant comprising the amino acid sequence of SEQ ID NO:5.

2. A conjugated mutant of an isolated human granulocyte-colony stimulating factor (G-CSF) comprising a mutant of a human G-CSF and a nonprotein chemical compound, wherein the mutant comprises the amino acid sequence of SEQ ID NO:5, and wherein the nonprotein chemical compound is attached to the cysteine residue at position 136 of SEQ ID NO:5.

3. The conjugated mutant of claim 2, wherein the mutant has a substitution at position 17 of SEQ ID NO: 5, the substitution replacing cysteine with serine.

4. The conjugated mutant of claim 2 or 3, wherein the nonprotein chemical compound is selected from the group consisting of polyethylene glycol (PEG), polyvinyl alcohol (PVA), polycarboxylic acid and polyvinyl pyrrolidone, binding with a compound selected from the group consisting of maleimide, vinyl sulfone, iodacetamide and orthopyridyl disulfide.

5. The conjugated mutant of claim 2 or 3, wherein the nonprotein chemical compound has a molecular weight in the range of about 2 to about 100 kDa.

6. The conjugated mutant of claim 4, wherein the PEG has a molecular weight in the range of about 5 to about 100 kDa.

* * * * *

```
                        SEQUENCE LISTING

<160> NUMBER OF SEQ ID NOS: 6

<210> SEQ ID NO 1
<211> LENGTH: 174
<212> TYPE: PRT
<213> ORGANISM: Artificial Sequence
<220> FEATURE:
<223> OTHER INFORMATION: Amino acid sequence of hG-CSF

<400> SEQUENCE: 1

Thr Pro Leu Gly Pro Ala Ser Ser Leu Pro Gln Ser Phe Leu Leu Lys
 1               5                  10                  15

Cys Leu Glu Gln Val Arg Lys Ile Gln Gly Asp Gly Ala Ala Leu Gln
             20                  25                  30

Glu Lys Leu Cys Ala Thr Tyr Lys Leu Cys His Pro Glu Glu Leu Val
         35                  40                  45

Leu Leu Gly His Ser Leu Gly Ile Pro Trp Ala Pro Leu Ser Ser Cys
     50                  55                  60

Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                 85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 2
<211> LENGTH: 175
<212> TYPE: PRT
<213> ORGANISM: Artificial Sequence
<220> FEATURE:
<223> OTHER INFORMATION: amino acid sequence of recombinant hG-CSF

<400> SEQUENCE: 2

Met Thr Pro Leu Gly Pro Ala Ser Ser Leu Pro Gln Ser Phe Leu Leu
```

```
        1               5                   10                  15
Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
                35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
 65                 70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
                115                 120                 125

Pro Ala Leu Gln Pro Thr Gln Gly Ala Met Pro Ala Phe Ala Ser Ala
                130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

<210> SEQ ID NO 3
<211> LENGTH: 174
<212> TYPE: PRT
<213> ORGANISM: Artificial Sequence
<220> FEATURE:
<223> OTHER INFORMATION: amino acid sequence of hG-CSF substituted with cysteine at the 133 position

<400> SEQUENCE: 3

```
Thr Pro Leu Gly Pro Ala Ser Ser Leu Pro Gln Ser Phe Leu Leu Lys
 1               5                   10                  15

Cys Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
                35                  40                  45

Leu Leu Gly His Ser Leu Gly Ile Pro Trp Ala Pro Leu Ser Ser Cys
        50                  55                  60

Pro Ser Gln Ala Leu Gln Leu Ala Gly Cys Leu Ser Gln Leu His Ser
 65                 70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
                100                 105                 110

Phe Ala Thr Thr Ile Trp Gln Gln Met Glu Glu Leu Gly Met Ala Pro
                115                 120                 125

Ala Leu Gln Pro Cys Gln Gly Ala Met Pro Ala Phe Ala Ser Ala Phe
                130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

<210> SEQ ID NO 4
<211> LENGTH: 174

```
<212> TYPE: PRT
<213> ORGANISM: Artificial Sequence
<220> FEATURE:
<223> OTHER INFORMATION: Amino acid sequence of hG-CSF substituted with
      cysteine at the 133th position and serine at the 17 position

<400> SEQUENCE: 4
```

Thr Pro Leu Gly Pro Ala Ser Ser Leu Pro Gln Ser Phe Leu Leu Lys
 1               5                  10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Cys Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

```
<210> SEQ ID NO 5
<211> LENGTH: 175
<212> TYPE: PRT
<213> ORGANISM: Artificial Sequence
<220> FEATURE:
<223> OTHER INFORMATION: Amino acid sequence of hG-CSF inserted with
      cysteine between the 135th and 136th position

<400> SEQUENCE: 5
```

Thr Pro Leu Gly Pro Ala Ser Ser Leu Pro Gln Ser Phe Leu Leu Lys
 1               5                  10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Cys Ala Met Pro Ala Phe Ala Ser Ala
    130                 135                 140

```
Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 6
<211> LENGTH: 175
<212> TYPE: PRT
<213> ORGANISM: Artificial Sequence
<220> FEATURE:
<223> OTHER INFORMATION: Amino acid sequence of hG-CSF inserted with
      cysteine between the 135th and 136th position and substituted
      with serine at the 17th position

<400> SEQUENCE: 6

Thr Pro Leu Gly Pro Ala Ser Ser Leu Pro Gln Ser Phe Leu Leu Lys
 1               5                  10                  15

Ser Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
        50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Cys Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```